United States Patent
Lin et al.

(10) Patent No.: US 7,746,455 B2
(45) Date of Patent: *Jun. 29, 2010

(54) TESTING SYSTEM FOR TESTING COLOR WHEELS

(75) Inventors: Hsin-Li Lin, Taipei Hsien (TW); I-Pen Chien, Taipei Hsien (TW); Kuang-Wei Lin, Taipei Hsien (TW); Po-Yuan Lai, Taipei Hsien (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 114 days.

This patent is subject to a terminal disclaimer.

(21) Appl. No.: 12/108,039

(22) Filed: Apr. 23, 2008

(65) Prior Publication Data

US 2009/0033922 A1 Feb. 5, 2009

(30) Foreign Application Priority Data

Aug. 1, 2007 (CN) .......................... 2007 1 0201230

(51) Int. Cl.
*G01B 11/26* (2006.01)
(52) U.S. Cl. .................... 356/141.1; 356/4.07; 356/418
(58) Field of Classification Search ................. 356/4.01, 356/4.07, 141.1, 152.2, 418; 359/891
See application file for complete search history.

(56) References Cited

U.S. PATENT DOCUMENTS

| | | | | |
|---|---|---|---|---|
| 6,637,890 B1 * | 10/2003 | Shiue et al. | .................... | 353/31 |
| 7,274,455 B2 * | 9/2007 | Ok et al. | ...................... | 356/417 |
| 2007/0081252 A1 * | 4/2007 | Lin et al. | ...................... | 359/618 |
| 2008/0002204 A1 * | 1/2008 | Xu et al. | ...................... | 356/418 |
| 2009/0097030 A1 * | 4/2009 | Ho et al. | ...................... | 356/418 |

FOREIGN PATENT DOCUMENTS

CN 101358840 A 2/2009

* cited by examiner

*Primary Examiner*—Isam Alsomiri
(74) *Attorney, Agent, or Firm*—Andrew C. Cheng (57) ABSTRACT

A testing system measures central angles of filter segments of a color wheel. The color wheel includes a color filter, which includes three sector-shaped filter segments and a motor for driving the filter segments to rotate. The testing system includes a sensor and a processor. The sensor emits light toward the color filter and receives light reflected back by the color filter, and generates an impulse signal according to intensity changes of the light reflected back by the color filter. The impulse signal includes a plurality of boundary impulses corresponding to boundaries formed between adjacent filter segments. The processor calculates central angles of the filter segments according to relationships between the boundary impulses.

8 Claims, 8 Drawing Sheets

(RELATED ART)

FIG. 8
(RELATED ART)

TESTING SYSTEM FOR TESTING COLOR WHEELS

CROSS-REFERENCE TO RELATED APPLICATION

This application is related to co-pending U.S. patent application entitled "TESTING METHOD FOR TESTING COLOR WHEELS" and filed on the same day as the instant application. The co-pending U.S. patent application is assigned to the same assignee as the instant application. The disclosure of the above-identified application is incorporated herein by reference.

BACKGROUND

1. Technical Field

The present invention generally relates to testing systems for testing color wheels, and particularly to a testing system for precisely measuring central angles of filter segments of a color wheel, and an angular position of a timing mark on the color wheel.

2. Description of Related Art

Figure 7:
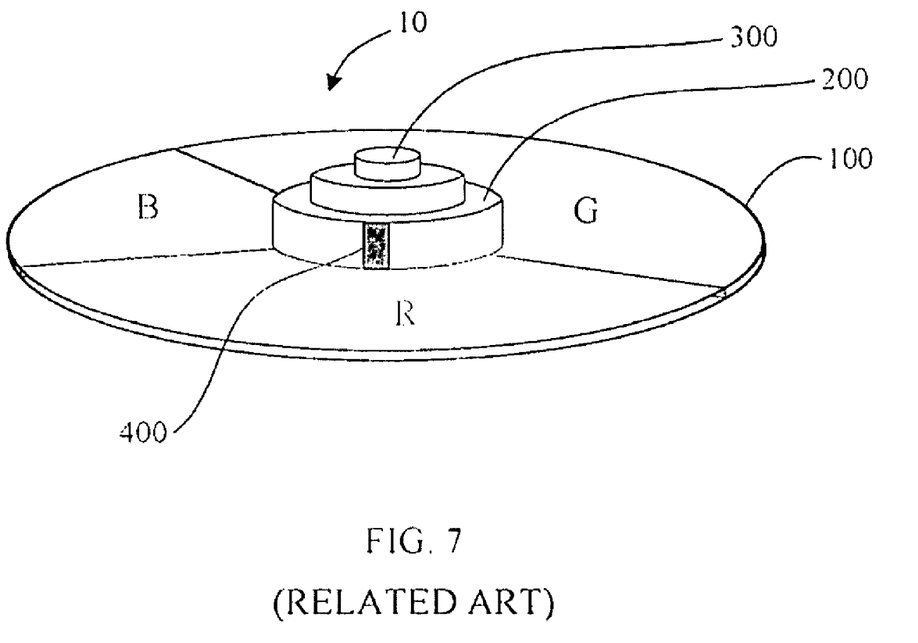
FIG. 7 is a schematic, isometric view of a color wheel of a projector system according to a related art.
Figure 8:
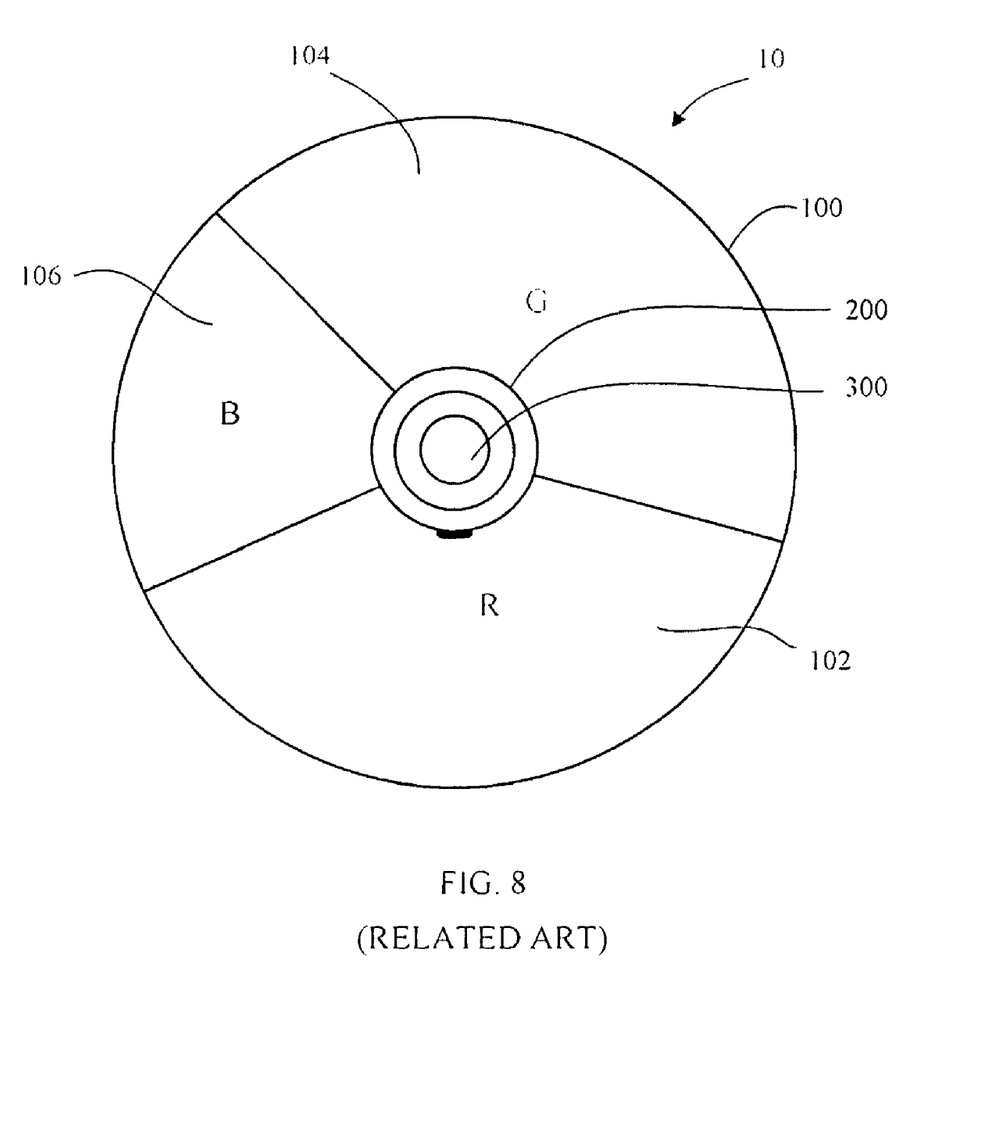
FIG. 8 is a top view of the color wheel of FIG. 7.

Referring to FIGS. 7 and 8, a color wheel 10 of a projector system is shown. The color wheel 10 includes a round color filter 100, a mounting portion 200, a motor 300 and a timing mark 400 adhered to a sidewall of the mounting portion 200. The color filter 100 is composed of three sector-shaped filter segments, i.e. red, green and blue filter segments 102, 104, 106. Because people perceive different colors with different reaction times, central angles of the red, green and blue filter segments 102, 104, 106 are designed to be different from each other. The timing mark 400 is arranged on the sidewall of the mounting portion 200.

In operation of the projector system, the color filter 100 and the timing mark 400 are driven by the motor 300 to rotate together. The central angles of the filter segments 102, 104, 106 and the angular position of the timing mark 400 relative to the filter segments 102, 104, 106 can be detected to help the projector system recognize positions of the filter segments 102, 104, 106. That is, the central angles of the filter segments 102, 104, 106 and the timing mark 400 help the projector system know which color is being shown in a display of the projector system at a given time. Therefore, the central angles of the filter segments 102, 104, 106 and the angular positions of the timing mark 400 are important parameters, which influence an image-forming quality of the projector system. If the central angles of the filter segments 102, 104, 106 and the actual angular position of the timing mark 400 relative to the filter segments 102, 104, 106 deviate seriously from predetermined central angles of the filter segments 102, 104, 106 and a predetermined angular position of the timing mark 400, the image-forming quality of the video will be greatly degraded.

SUMMARY

A testing system for precisely measuring central angles of filter segments of a color wheel is provided. The color wheel includes a color filter, which includes three sector-shaped filter segments and a motor for driving the filter segments to rotate. The testing system includes at least a sensor and a processor. The sensor is configured for emitting light toward the color filter and receiving light reflected back by the color filter, and further generating an impulse signal according to intensity changes of the light reflected back by the color filter. The impulse signal includes a plurality of boundary impulses corresponding to boundaries formed between adjacent filter segments. The processor is configured for calculating central angles of the filter segments according to relationships between the boundary impulses.

Other advantages and novel features of the present testing system will become more apparent from the following detailed description of preferred embodiments when taken in conjunction with the accompanying drawings.

DETAILED DESCRIPTION OF THE EMBODIMENTS

Reference will now be made to the drawing figures to describe the various present embodiments in detail.

Presently, there are many kinds of color filters, such as RGB color filters, RGB and white color filters, and RGBRGB color filters. Hereinafter, an RGB color wheel is taken as an example to describe the testing system.

Figure 1:
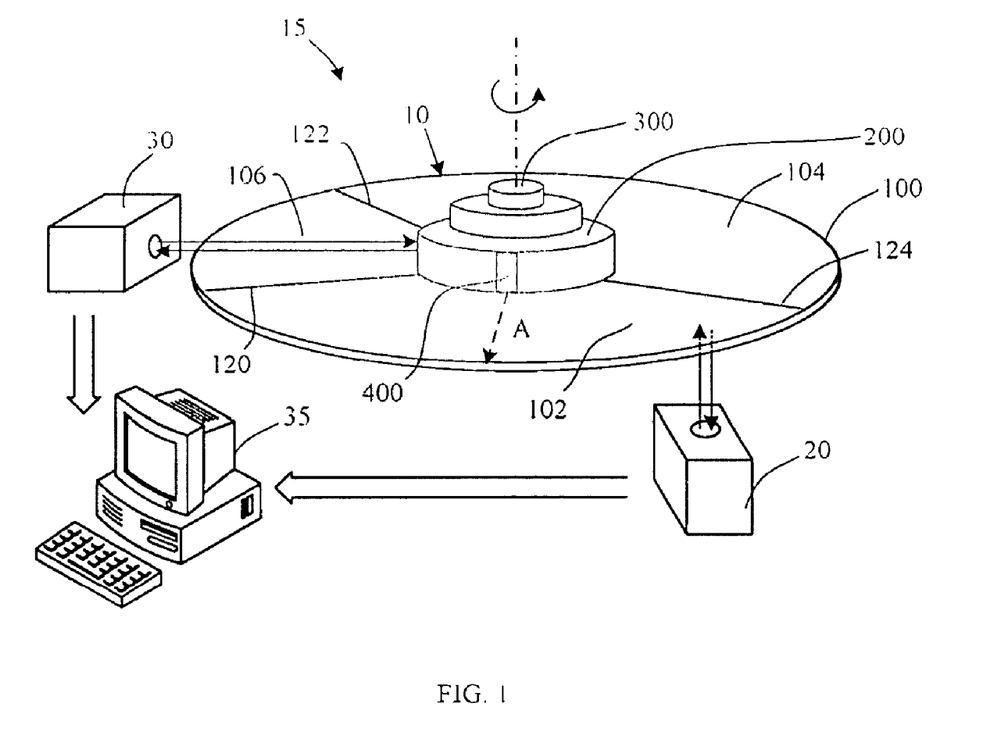
FIG. 1 is a schematic view of a testing system according to a first embodiment of the present invention.

Referring to FIG. 1, an RGB color wheel 10 includes a round color filter 100, a mounting portion 200, a motor 300, and a timing mark 400 on a sidewall of the mounting portion 200. The timing mark 400 has a different reflectivity characteristic than the sidewall, which is accomplished by the timing mark 400 being of a different color or having a different surface finish than the sidewall. The color filter 100 comprises three sector-shaped filter segments, i.e. red, green and blue filter segments 102, 104, 106. The filter segments 102, 104, 106 of the color filter 100 may have different central angles from each other. Three boundaries 120, 122, 124 are formed between adjacent filter segments 102 and 106, 106 and 104, 104 and 102 of the color wheel 10, respectively.

The testing system 15 includes a first sensor 20, a second sensor 30, and a processor 35. The first and second sensors 20, 30 emit light toward the color wheel 10 and receive light reflected back by the color wheel 10, and further generate impulse signals according to intensity changes of the received light.

The first sensor 20 is located just below the color filter 100. During operation of the testing system 15, the color filter 100 rotates uniformly with the motor 300, and the first sensor 20 emits light toward the color filter 100. Some of the light is reflected back by the filter segments 102, 104, 106 of the color filter 100 and received by the first sensor 20. Since each of the filter segments 102, 104, 106 only allows light of a corresponding color to pass through, the intensities of the light reflected back by the different filter segments 102, 104, 106 of the color filter 100 are different from each other. The intensity of the reflected light, which is received by the first sensor 20, accordingly changes during rotation of the color wheel 10.

The first sensor 20 detects the intensity changes of the reflected light and accordingly generates a first impulse signal 40.

Figure 2:
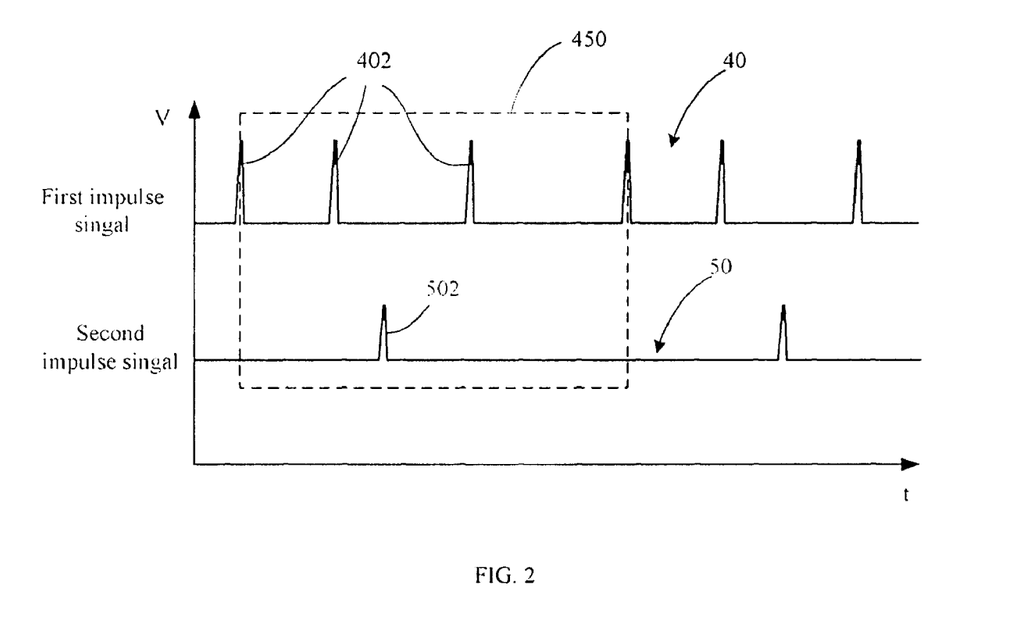
FIG. 2 is a waveform diagram of impulse signals generated by the testing system of FIG. 1.

Referring to FIG. 2, the first impulse signal 40 includes three peaks, i.e. three boundary impulses 402, in one time period 450. The boundary impulses 402 are generated by the first sensor 20 corresponding to the reflected lights at the boundaries 120, 122, 124 between the filter segments 102, 104, 106. A time period 450 is defined by a time interval between two boundary impulses 402 of the first impulse signal 40. In this embodiment, the time period 450 is defined by a time interval between four adjacent peaks of the first impulse signal 40. During one time period 450, the color filter 100 rotates about 360 degrees, which equals the sum of the central angles of the red, green and blue filter segments 102, 104, 106. Therefore, a proportion of time intervals defined between each two adjacent boundary impulses 402 of one time period 450 substantially equals a proportion of the central angles of the red, green and blue filter segments 102, 104, 106. Thus, the central angles of the red, green and blue filter segments 102, 104, 106 can be calculated accordingly.

The second sensor 30 faces the sidewall of the mounting portion 200. During rotation of the color wheel 10, the second sensor 30 emits light toward the sidewall of the mounting portion 200 on which the timing mark 400 is located. The light is reflected back from the sidewall of the mounting portion 200 and the timing mark 400, and is received by the second sensor 30. Since the light reflected by the sidewall of the mounting portion 200 is different from that of the timing mark 400, accordingly, the light received by the second sensor 30 changes during the rotation of the color wheel 10. The second sensor 30 detects the intensity changes of the reflected light and accordingly generates a second impulse signal 50.

Referring to FIG. 2, the second impulse signal 50 includes a peak, i.e. a time impulse 502, in one time period 450. The time impulse 502 is generated by the second sensor 30 corresponding to the light reflected by the timing mark 400. In the time period 450, a proportion of time intervals between the time impulse 502 and each boundary impulse 402 is substantially equal to a proportion of angles formed between the timing mark 400 and each boundary 120, 122, 124 of the color wheel 10. In this embodiment, the angle formed between the timing mark 400 and each boundary 120, 122, 124 of the color wheel 10 is defined between a radius A of the color wheel 10 corresponding to the timing mark 400 and each boundary 120, 122, 124 of the color wheel 10. The angles formed between the timing mark 400 and the boundaries 120, 122, 124 of the color wheel 10, i.e. position angles of the timing mark 400, can thus be calculated. The angular position of the timing mark 400 is therefore obtained.

The processor 35 is used for calculating the central angles of the red, green and blue filter segments 102, 104, 106 and the angular position of the timing mark 400 according to the principles disclosed above.

In the testing system 15, the first and the second sensors 20, 30 emit light toward the color wheel 10, and generate the first and the second impulse signals 40, 50 after the light reflected by different portions of the color wheel 10 is received by the first and the second sensors 20, 30. The central angles of the filter segments 102, 104, 106 of the color filter 100 and the angular position of the timing mark 400 are calculated according to the first and the second impulse signals 40, 50. By ensuring that the calculated central angles of the filter segments 102, 104, 106 and the angular position of the timing mark 400 meet certain predetermined criteria, imaging quality of a projector system using the color wheel is assured.

Figure 3:
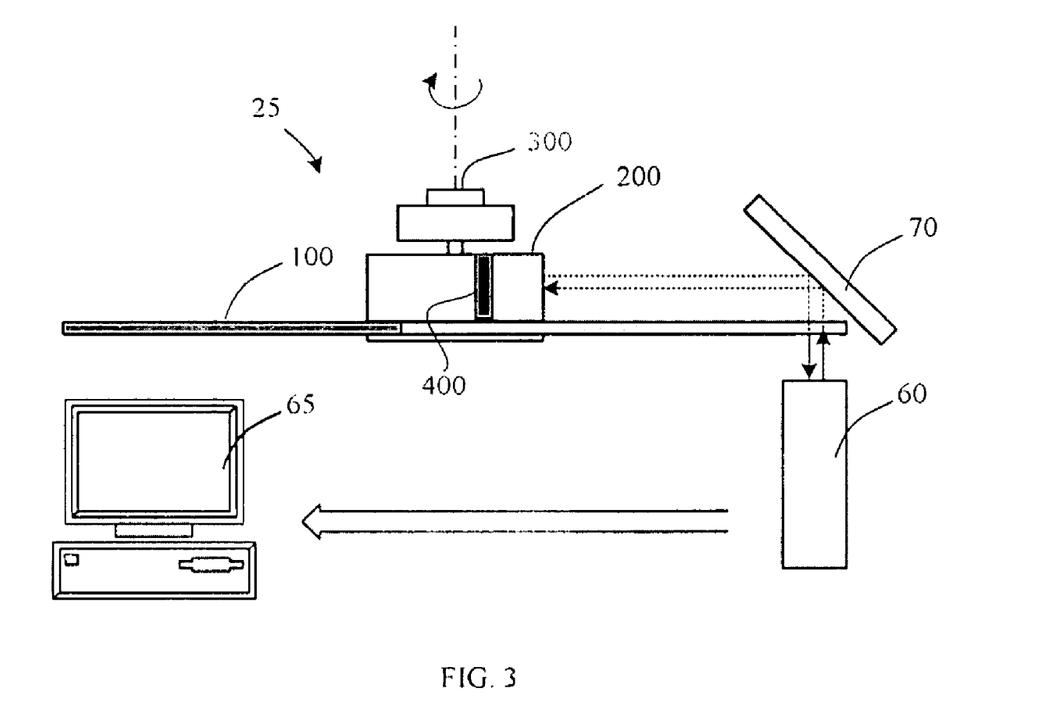
FIG. 3 is a schematic view of a testing system according to a second embodiment of the present invention.

Referring to FIG. 3, a second embodiment of the present testing system 25 is shown. The testing system 25 includes a third sensor 60, a reflector 70, and a processor 65. The third sensor 60 is located just below the color filter 100, and emits light toward the filter segments 102, 104, 106 during the rotation of the color wheel 10. Some of the light emitted from the third sensor 60 is reflected back by the filter segments 102, 104, 106, and the remaining light passes through the filter segments 102, 104, 106. The light passed through the filter segments 102, 104, 106 is reflected toward the sidewall of the mounting portion 200 by the reflector 70, which faces toward the sidewall of the mounting portion 200 at a 45 degree angle with respect to the color filter 100 of the color wheel 10. The light reflected toward the sidewall of the mounting portion 200 is reflected back to the reflector 70, which then reflects the light to the color filter 100. Then, the reflected light passes through the filter segments 102, 104, 106 and is received by the third sensor 60. The third sensor 60 generates a third impulse signal 80 according to intensity changes of the reflected light.

Figure 4:
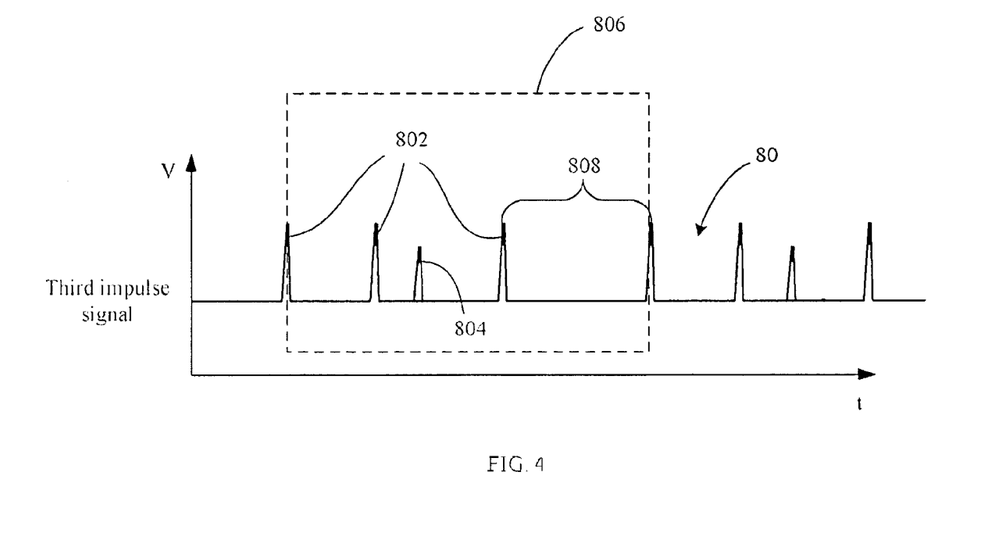
FIG. 4 is a waveform diagram of an impulse signal generated by the testing system of FIG. 3.

Referring to FIG. 4, the third impulse signal 80 includes four peaks, i.e. three boundary impulses 802 and a time impulse 804, in one time period 806. The time period 806 is defined by a time interval between two uniform/equal peaks of the third impulse signal 80. A time span 808 is defined as the time interval between adjacent peaks of the time period 806. In FIG. 4, a first peak and a last peak of five adjacent peaks of the third impulse signal 80 are found to be uniform/equal and therefore define the time period 806. A proportion of time spans 808 of the time period 806 substantially equals a proportion of a corresponding angle of the angles formed between adjacent boundaries 122 and 120, 124 and 122, or between the timing mark 400 and adjacent boundaries 120, 124. The angular position of the timing mark 400 and the central angles can be calculated by the processor 65 accordingly. For example, if a proportion of the time intervals 808 of the time period 806 is 3:1:3:5, the angle formed between the boundaries 122 and 120 equals 90 degrees, the angle formed between the boundary 120 and the timing mark 400 equals 30 degrees, the angle formed between the timing mark 400 and the boundary 124 equals 90 degrees, and the angle formed between the boundaries 124 and 122 equals 150 degrees.

Figure 5:
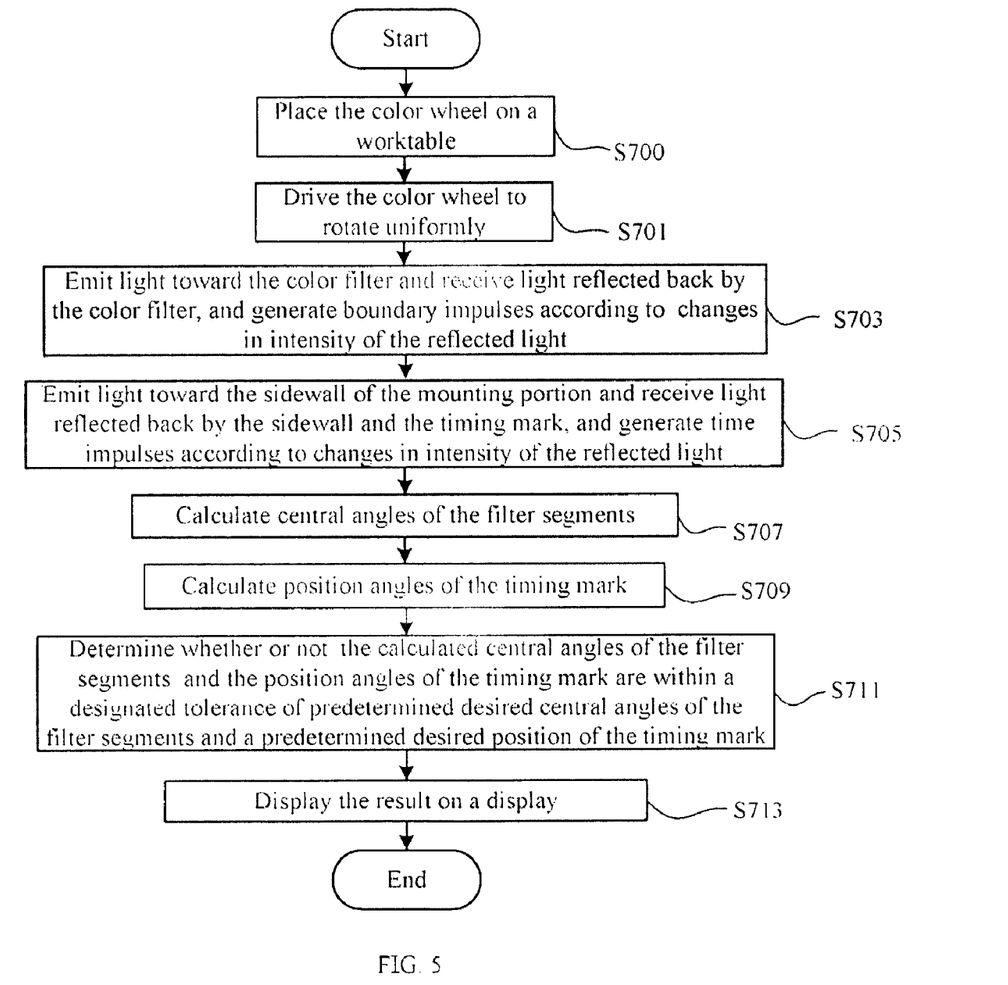
FIG. 5 is a flow chart of a testing method according to the first embodiment of the present invention.

Referring to FIG. 5, a flow chart of a first embodiment of a method for testing a color wheel is shown. The first embodiment of the method corresponds to the testing system 15 shown in FIGS. 1 and 2, and includes the following steps:

Step S700: Place the color wheel 10 on a worktable.

Step S701: Use the motor 300 to drive the color filter 100 and the mounting portion 200 to rotate together at a uniform speed.

Step S703: Emit light toward the color filter 100 of the color wheel 10, receive light reflected back by the color filter 100, and generate a first impulse signal 40 according to intensity changes of the reflected light. The first impulse signal 40 includes three boundary impulses 402 in one time period 450. The boundary impulses 402 are generated according to the light reflected back by the boundaries 120, 122, 124 of the color filter 100.

Step S705: Emit light toward the sidewall of the mounting portion 200 on which the timing mark 400 is located, receive light reflected back by the sidewall of the mounting portion 200 and the timing mark 400, and generate a second impulse signal 50 according to intensity changes of the reflected light. The second impulse signal 50 includes a time impulse 502 in one time period 450. The time impulse 502 is generated according to the light reflected back by the timing mark 400.

Step S707: Calculate central angles of the filter segments 102, 104, 106 of the color filter 100 according to time intervals between the boundary impulses 402 of the first impulse signal 40.

Step S709: Calculate angles formed between the timing mark 400 and each of the boundaries 120, 122, 124 of the color filter 100, i.e. position angles of the timing mark 400, according to time intervals between the time impulse 502 of the second impulse signal 50 and the boundary impulses 402 of the first impulse signal 40. The angular position of the timing mark 400 on the color wheel 10 is obtained.

Step S711: Determine whether or not the calculated central angles of the filter segments 102, 104, 106 and the position angles of the timing mark 400 are within a designated tolerance of predetermined desired central angles of the filter segments 102, 104, 106 and a predetermined desired position of the timing mark 400, respectively, to decide whether the color wheel 10 satisfies quality requirements.

Step S713: Display the result on a display of the processor 35.

In the above steps, Steps S703 and S705 can be interchanged, i.e. Step S705 can be performed before Step S703, or Steps S703 and S705 can be executed simultaneously.

Figure 6:
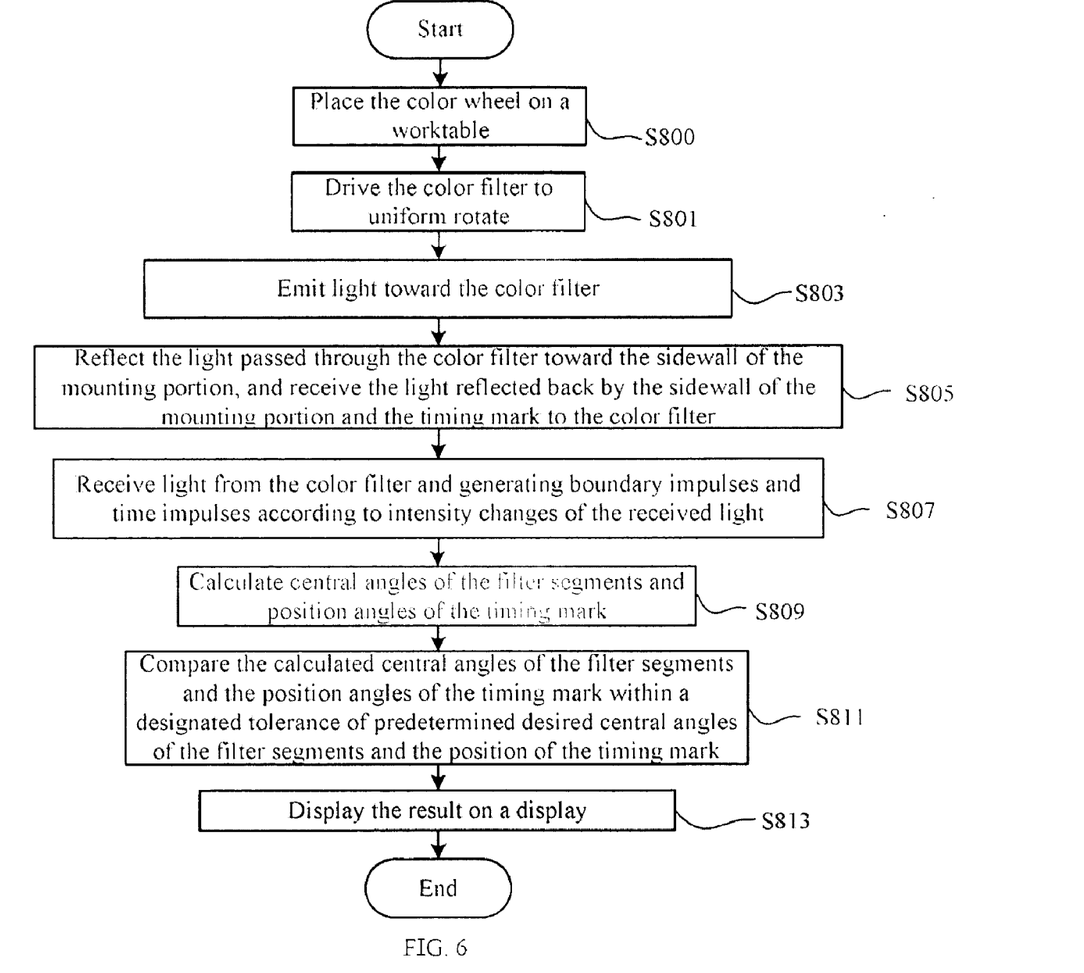
FIG. 6 is a flow chart of a testing method according to the second embodiment of the present invention.

Referring to FIG. 6, a flow chart of a second embodiment of the method is shown. The second embodiment of the method corresponds to the testing system 25 shown in FIGS. 3 and 4, and includes the following steps:

Step S800: Place the color wheel 10 on a worktable.

Step S801: driving the color filter 100 to rotate at a uniform speed.

Step S803: Emit light toward the color filter 100 of the color wheel 10.

Step S805: Reflect the light passed through the color wheel 10 toward the sidewall of the mounting portion 200 on which the timing mark 400 is located, and reflect the light reflected from the sidewall of the mounting portion 200 and the timing mark 400 to the color filter 100.

Step S807: Receive the light from the color filter 100 and generate an impulse signal 80 according to intensity changes of the received light. The light from the color wheel 10 includes two kinds of light, i.e. the light directly reflected back by the color filter 100, and the light that passes through the color filter 100 after having been reflected by the sidewall of the mounting portion 200 and the timing mark 400. The impulse signal 80 includes a plurality of boundary impulses 802 which are generated according to the light reflected by the boundaries of the color filter 100, and a plurality of time impulses 804 which are generated according to the light reflected by the timing mark 400.

Step S809: Calculate central angles of the filter segments 102, 104, 106 of the color filter 100 and the angles formed between the timing mark 400 and the filter segments 102, 104, 106 according to relationships between the boundary impulses 802 and the time impulse 804 of the impulse signal 80. The central angles of the filter segments 102, 104, 106 of the color filter 100 are calculated according to time intervals between the boundary impulses 802. The angles formed between the timing mark 400 and the filter segments 102, 104, 106, i.e. position angles of the timing mark 400, are calculated according to time intervals between the time impulse 804 and the boundary impulses 802. The angular position of the timing mark 400 on the color wheel 10 is obtained.

Step S811: Determine whether or not the calculated central angles of the filter segments 102, 104, 106 and the position angles of the timing mark 400 are within a designated tolerance of predetermined central angles of the filter segments 102, 104, 106 and a predetermined position of the timing mark 400, respectively, to decide whether the color wheel 10 satisfies a quality requirement.

Step S813: Display the result on a display of the processor 35.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A testing system configured for testing a color wheel, the color wheel comprising a color filter comprising several sector-shaped filter segments and a motor for driving the filter segments of the color filter to rotate, the testing system comprising:

at least a sensor configured for emitting light toward the color filter and receiving light reflected back by the color filter, and generating an impulse signal according to intensity changes of the light reflected back by the color filter, the impulse signal comprising a plurality of boundary impulses corresponding to boundaries formed between adjacent filter segments; and a processor configured for calculating central angles of the filter segments according to relationships between the boundary impulses.

2. The testing system of claim 1, wherein the processor calculates out central angles of the filter segments due to time intervals between the boundary impulses and a total degree of the central angles of the filter segments.

3. The testing system of claim 2, wherein the color wheel further comprises a timing mark co-rotated with the filter segments, the at least a sensor generates a time impulse corresponding to the timing mark, and the processor calculates an angular position of the timing mark on the color wheel according to time intervals between the boundary impulses and the time impulse.

4. The testing system of claim 3, wherein the timing mark is located on a sidewall of the color wheel, the at least a sensor emits light toward the filter segments, some of the light is directly reflected back by the filter segments and received by the at least a sensor, some of the light passes through the filter segments and is reflected toward the sidewall of the color wheel by a reflector, reflected back by the sidewall of the color wheel and the timing mark, reflected toward the color wheel by the reflector, passes through the filter segments and is received by the at least a sensor.

5. The testing system of claim 4, wherein the reflector forms a 45-degree angle with respect to the color filter.

6. The testing system of claim 3, wherein the timing mark is attached to a sidewall of the color wheel, the at least a sensor comprises a first sensor and a second sensor, the first sensor emits light toward the filter segments and generates the boundary impulse, and the second sensor emits light toward the sidewall of the color wheel and generates the time impulse.

7. The testing system of claim 6, wherein the first sensor is located just below the color filter, and the second sensor faces the sidewall.

8. The testing system of claim 1, wherein the color filter rotates with the motor at a uniform speed.

* * * * *